United States Patent [19]

Smith

[11] Patent Number: 5,398,677

[45] Date of Patent: Mar. 21, 1995

[54] CONDENSATION COLLECTOR FOR RESPIRATION SYSTEM

[76] Inventor: Charles A. Smith, 811 Starlite Dr., Louisville, Ky. 40207

[21] Appl. No.: 907,113

[22] Filed: Jul. 27, 1993

[51] Int. Cl.⁶ .......................................... A61M 16/00
[52] U.S. Cl. ...................... 128/205.12; 128/205.27
[58] Field of Search ................. 128/205.27, 205.12, 128/205.24, 912

[56] References Cited

U.S. PATENT DOCUMENTS

| | | | |
|---|---|---|---|
| 3,454,005 | 7/1969 | Eubanks et al. | 128/205.12 X |
| 3,620,228 | 11/1971 | Schmid | 137/237 |
| 3,968,812 | 7/1976 | Eross | 128/205.12 X |
| 4,457,305 | 7/1984 | Shanks et al. | 128/205.12 |
| 4,627,460 | 12/1986 | Eising | 137/192 |
| 4,867,153 | 9/1989 | Lorenzen et al. | 128/205.12 |
| 4,997,463 | 3/1991 | Ricciardelli | 55/165 |
| 5,168,868 | 12/1992 | Hicks | 128/205.12 |

FOREIGN PATENT DOCUMENTS

| | | | |
|---|---|---|---|
| 3742888 | 7/1989 | Germany | 128/205.12 |
| 3823242 | 2/1990 | Germany | 128/205.12 |
| 9114476 | 10/1991 | WIPO | 128/205.12 |

Primary Examiner—Edgar S. Burr
Assistant Examiner—Eric P. Raciti

[57] ABSTRACT

A condensation collector for inhalation and exhalation conduits as used for anesthesia or other respiratory support purposes, comprises a container having a top inlet, a condensate collection chamber having a bottom outlet constituting a valve seat which bottom outlet is connected to the container inlet, and a buoyant ball or other valve closure member disposed in the collection chamber and movable between a closed position sealing the valve seat and an open position floating on accumulated condensate above the valve seat. The condensate collection chamber is above the valve closure member in fluid communication with either the inhalation or the exhalation conduits.

17 Claims, 3 Drawing Sheets

CONDENSATION COLLECTOR FOR RESPIRATION SYSTEM

BACKGROUND OF THE INVENTION

In a respiration support system as utilized in a hospital, a nursing home, or other health care facility, warm, humidified air is supplied to a patient through an inhalation conduit. The inhalation conduit is usually a flexible, corrugated hose made of polymeric resinous material such as polypropylene, polyethylene, polystyrene and the like. The ambient air encompassing the inhalation conduit is usually appreciably cooler than the humidified air supplied to the patient. As a consequence, water vapor tends to condense inside the inhalation hose. The same phenomenon occurs in the exhalation conduit that is usually employed as a return conduit from the patient to the ventilator and humidifier apparatus of the system. The air flow to the patient or from the patient can be blocked if enough of this "rainout" condensate accumulates so that the lower portion of one of the inhalation and exhalation conduits is filled. The hoses connected to a patient cannot be placed under tension, as it is necessary to accomodate the patient as he changes position.

With this "rainout" condensation occurring on a continuous basis, attending personnel must drain the breathing hoses regularly and frequently so that the breathing of the patient can continue uninterrupted. Previously known solutions to this problem have not been particularly satisfactory. Thus, it has become customary to utilize small reservoirs attached directly to each of the inhalation and exhalation conduits. Reservoirs of this kind soon become too heavy for the conduits to support, as the condensate collects in them, so they must be emptied frequently. Alternatively, relatively expensive and complicated pressure activated valves for draining accumulation of the condensate into larger containers have been employed.

SUMMARY OF THE INVENTION

It is a principal object of the invention, therefore, to provide a new and improved condensation collector for use with the inhalation and exhalation conduits of a respiratory support system that is simple, inexpensive, and reliable, and that requires no additional power or pressure sources.

A further object of the invention is to provide a new and improved condensation collector for the inhalation and exhalation conduits of a respiratory support system that is safe in operation, saves time for the monitoring personnel, and permits accurate measurement of collected condensate from the respiration system.

Accordingly, the invention relates to a condensation collector for removing condensate of predetermined density from at least one of the inhalation and exhalation conduits of a respiratory support system comprising a ventilator/humidifier apparatus having a fresh air make-up inlet, a return inlet, an outlet, an inhalation conduit for connecting the ventilator/humidifier outlet to a patient, an exhalation conduit for connecting the patient back to the ventilator/humidifier return inlet, and two condensate discharge connections, each interposed in one of the conduits. The condensation collector comprises a condensation container having an inlet adjacent the top of the container, a condensate collection chamber having a bottom outlet connected to the condensation container inlet, and a buoyant valve closure member, having a density less than said predetermined density diposed within the collection chamber for movement between a closed position in which the closure member closes the bottom outlet of the collection chamber and an open position in which the closure member floats on accumulated condensate above the bottom outlet. The collector further comprises at least one of the condensate discharge connections to the condensate collection chamber, above the valve closure member.

DESCRIPTION OF THE PREFERRED EMBODIMENTS

Figure 1:
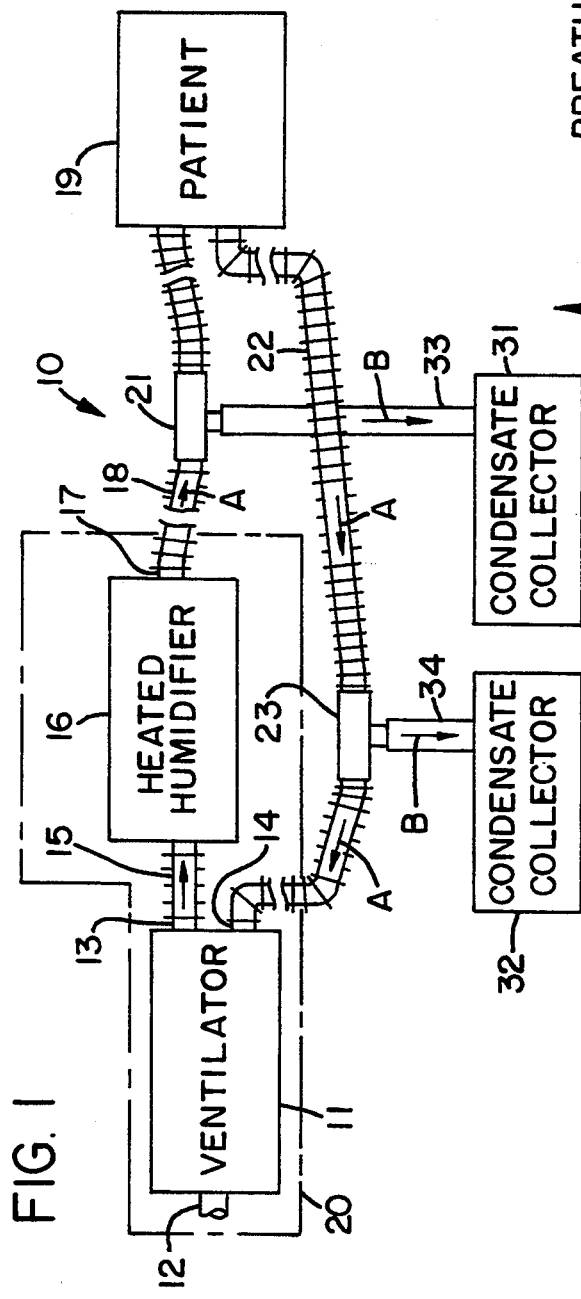
FIG. 1 is a schematic block diagram of a respiratory support system incorporating a condensation collector according to one embodiment of the present invention.

The respiratory support system 10 illustrated in FIG. 1 comprises a ventilator/humidifier apparatus 20 that includes a ventilator 11 having a fresh air makeup inlet 12, an outlet 13, and a return inlet 14. The outlet 13 of ventilator 11 is connected by a short hose or other conduit 15 to the inlet of a heated humidifier 16. Humidifier 16 has an outlet 17 (the outlet of apparatus 20) that is in turn connected by an inhalation conduit 18 to a patient 19. There is a condensate discharge connection 21 connected in series in the inhalation hose 18; the discharge connection 21 is shown as a simple T fitting.

System 10 further includes an exhalation conduit or hose 22. Hose 22 extends from the patient 19 back to the return inlet 14 of ventilator 11. As with .inhalation conduit 18, exhalation conduit 22 has a condensate discharge connection 23 connected in series therewith. Connection 23, like connection 21, is shown as a simple T fitting in hose 22. In many sytems, the inhalation and exhalation conduits 18 and 22 are combined, at patient 19, in a single Y piece which affords a connection for inhalation conduit 18 and exhalation conduit 22 with the patient 19. Because such an arrangement is conventional, it has not been illustrated in FIG. 1.

Respiration system 10, FIG. 1, further comprises two condensate collectors 31 and 32. A hose or other conduit 33 connects the first condensate discharge connection 21 preferably a T fitting in inhalation line 18, to the first collector 31. Similarily, another hose or conduit 34 connects the other T fitting 23 in exhalation line 22 to the other condensate collector 32.

Operation of the respiration system 10 of FIG. 1 is quite conventional, apart from the condensate collectors 21 and 32. Air, which may be mixed with an anesthetic or with a therapeutic gas, enters ventilator 11 through make up inlet 12 and is pumped into the heated humidifier 16 through conduit 15. From the outlet 17 of the ventilator/humidifier apparatus 20 of system 10, this air is supplied to patient 19, under limited pressure, through the inhalation conduit 18 in pressurized pulses as indicated by the pulses 40 in FIG. 2. During each breathing cycle 41 the patient inhales during the inspiration period 42 of the cycle and exhales during the longer exhalation period 43 of the cycle. When the patient exhales, the air from the patient is piped back to the return inlet 14 of ventilator 11 through the flexible corrugated exhalation conduit 22, FIG. 1.

In sustained operation of system 10, because the ambient air around hose 18 is substantially cooler than that within the hose, the water and other vapor in the air within the conduit condenses. The condensate tends to flow toward the condensate discharge connection 21, which is located at or near the low point for hose 18. Similarily, water vapor in the air exhaled by the patient condenses in hose 22 and flows toward the T fitting 23, which is again located at or near the low point of exhalation conduit 22. The condensate from the inhalation and exhalation conduits 18 and 22 flows, as generally indicated by arrows B, into the two condensate collectors 31 and 32, respectively. Air flow within the system is indicated by arrows A.

Figure 3:
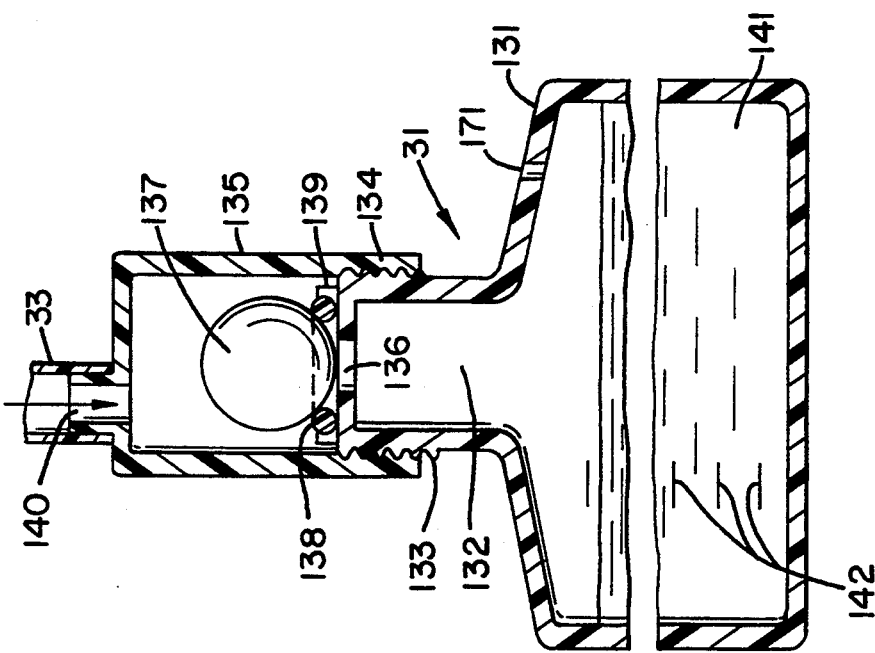
FIG. 3 is a sectional elevation view of one embodiment of a condensation collector constructed in accordance with the invention.

A preferred construction for the condensate collector 31 of FIG. 1 is illustrated in FIG. 3. The condensation collector 31 shown in FIG. 3 comprises a condensation container 131, which may constitute a plastic container like a one gallon milk bottle. Container 131 has an inlet neck 132 at the top of the container. The upper end of neck 132 has an external thread 133 onto which the threaded portion 134 of a condensate collection chamber 135 is mounted. Condensation chamber 135 has a bottom outlet 136 opening into the inlet neck 132 of container 131.

A buoyant valve closure member in the form of a ball 137 is disposed within the condensate collection chamber 135. Ball 137 should have a density appreciably less than the density of water and certainly less than the density of the condensate accumulated from hose 18 of sytem 10 (FIG. 1) A ping-pong ball, which weighs about two grams, is acceptable. Ball 137 is shown resting upon an O-ring 138 that affords a valve seat encompassing the outlet opening 136. This is the closed position for the valve closure member, ball 137. The valve closure ball stays in this position as long as the accumulated condensate 139 in chamber 135 is at a relatively low level as shown in FIG. 3. At the top of chamber 135 there is an inlet opening 140 on which the condensate conduit 33 is mounted. A small vent 171 is provided in container 131.

Operation of condensation collector 31, FIG. 3, is quite simple. Water and other condensate from the inhalation conduit 18 of system 10 (FIG. 1) flows into chamber 135 by gravity through conduit 33 and inlet 140. The condensate 139 collects in pool at the bottom of chamber 135. With continued operation of the respiratory support system 10, of FIG. 1, the level of condensate 139 within chamber 135 rises to an extent sufficient to lift the valve closure member, ball 137, above the valve seat afforded by O-ring 138. When this happens, the excess condensate 139 from pool in chamber 135 flows down through the neck 132 of bottle 131 and is collected therein as indicated at 141. If desired, container 131 may be provided with a graduated scale 142 to delineate the quantity of condensate collected from the inhalation hose 18 of system 10. Of course, when the level of condensate in chamber 135 is reduced appreciably, ball 137 settles back down onto seat 138 and operation continues as previously described.

The single-source condensate collector 32, FIG. 1, may duplicate the collector 31 of FIG. 3 in construction and in operation.

Figure 4:
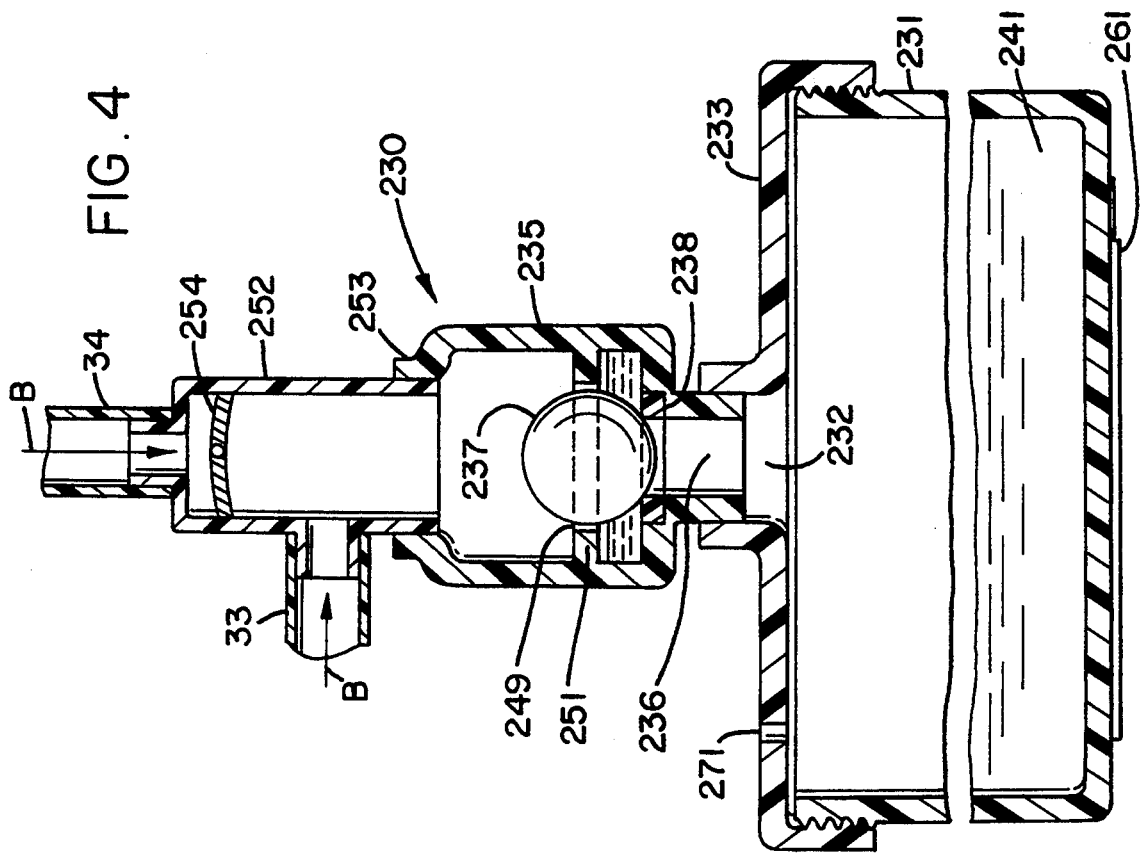
FIG. 4 is a sectional elevation view of a preferred embodiment of a condensation collector according to the invention.

FIG. 4 illustrates a condensation collector 230, constructed in accordance with another embodiment of the invention, that replaces both collectors 31 and 32 in system 10, FIG. 1. Device 230 includes a condensation container 231 which again by be a relatively large (one gallon) plastic container. In this instance container 231 is covered by a lid 233 affording in inlet 232 at the top of the container. The inlet 232 is in direct communication with the outlet 236 at the bottom of a condensate collection chamber 235. Within chamber 235 there is a buoyant valve closure member, shown as a ball 237, that normally rests upon a valve seat 238 at the top rim of outlet 236. Valve seat 238 is shown in an alternative embodiment as an aperatured flat elastomer washer, instead of the O-ring shown in FIG. 3. Ball 237 is disposed within a central opening 249 in a guide member 251 that projects into chamber 235. Guide member 251 may be a separate member but is shown as an integral part of collection chamber 235. As before, an ordinary ping pong ball can be used as valve member 237.

A valve housing 252 extends down into and is joined to the open upper end 253 of condensate collection chamber 235. A pressure actuated flapper valve 254 is located in the upper portion of housing 252. One inlet for condensation collector 230 is located above valve 254 and is connected to the exhalation condensate conduit 34. The other inlet is located below valve 254 and is connected to the conduit 33 from inhalation line 18, FIG. 1.

The operation of condensation collector 230, FIG. 4, is similar to that of the previously described collector 31 of FIG. 3. Thus, condensate from the inhalation and exhalation conduits of system 10 (FIG. 1) flows into the valve housing 252 which is an upper extension of chamber 235 through the conduits or hoses 33 and 34. The flow from conduit 34 is permitted to pass into housing 252 and thence into chamber 235 when there is appreciable condensate accumulation in conduit 33, which occurs in the inhalation portion of the operating cycle for system 10 (see FIG. 2). The flow from exhalation conduit 22, through hose 34, on the other hand, is open and free to flow except when stopped by valve 254, which is held closed by pressure from conduit 33 (from hose 18) during the exhalation portion of each breathing cycle.

As before, the condensate collects in a pool 239 around the bottom of valve closure member 237, in chamber 235. When the level of the condensate pool 239 gets high enough, the buoyant valve member 237 is lifted, opening outlet 236 and allowing flow of the condensate into container 231. There it collects in a pool 241. When the level of the initial collection pool 239 gets high enough, the buoyant valve member 237 is lifted, opening outlet 236 and allowing flow of the condensate into container 231. There it collects in a pool 241. When the level of the initial collection pool 239 goes down sufficiently, ball 237 again closes valve seat 238 and a further accumulation cycle occurs. There is a small vent 271 in lid 233 so that container 231 is at ambient pressure. As is shown in FIG. 4, valve seat 238 need not be a round O-ring as in FIG. 3, but may be a flat apertured elastomer washer.

Figure 2:
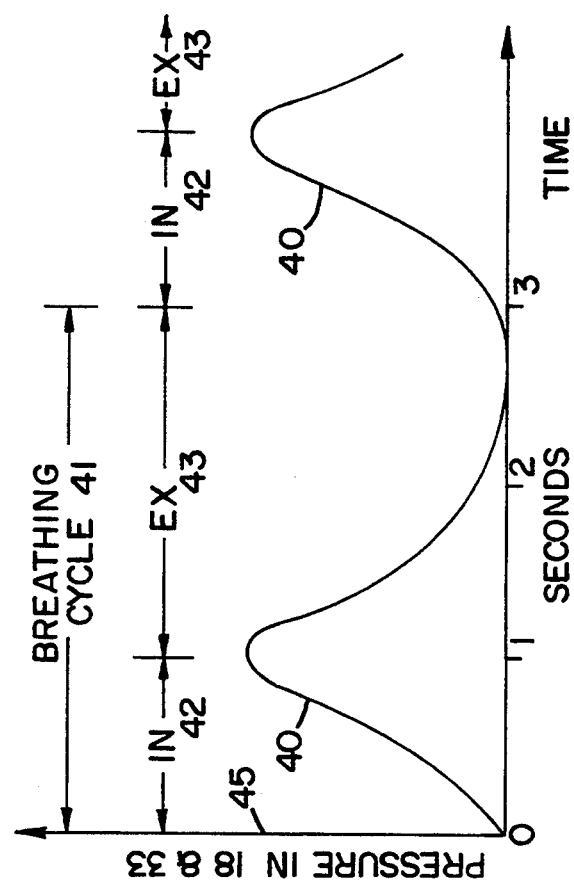
FIG. 2 illustrates a breathing cycle in a respiratory support system.

In FIGS. 2 and 3, containers, housings, and conduits are all shown as being formed of polymeric resinous materials, and this is usually preferred. However, it should be understood that other materials can be utilized as desired. Thus, either of the condensate containers 131 and 231 could be a glass bottle. Other elements of each of the two condensation collectors 31 (or 32) might be formed of metal or other materials. A base 261 can be formed on any of the condensation containers, as shown in FIG. 4, and may be desirable to keep the condensation collector in one position. As previously noted, corrugated hoses may be used for any of the conduits shown in the various figures; that is the usual construction. Conduits 33 and 34, however, are preferably smooth tubing. If desired, a disinfectant may be put into either of the containers 131 and 231 to disinfect the collected condensate so as not to pose a contamination hazard to attending personnel should a spill occur.

Figure 5:
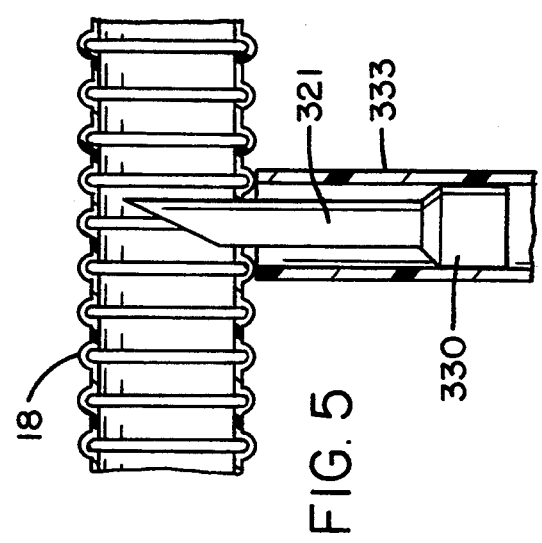
FIG. 5 is a detail view, partly in cross section, of a modification of the invention.

FIG. 5 illustrated a modification of the respiratory support system 10 that may be utilized to eliminate the T connections 21 and 23, FIG. 1. In the detail view of FIG. 5, the condensate conduit 333, which replaces tube 33 of the previously described apparatus, is equipped with a probe or spike 321 at the end of conduit 333 to be connected to inhalation conduit 18. As shown in FIG. 5 the hollow spike 321 is used to penetrate the wall of conduit 18; this connection should be made at or near the low point of the inhalation conduit to facilitate effective condensate drainage through tube 333. Of course, the connection spike or probe 321 should be sealed into tube 333 as indicated at 330.

Figure 6:
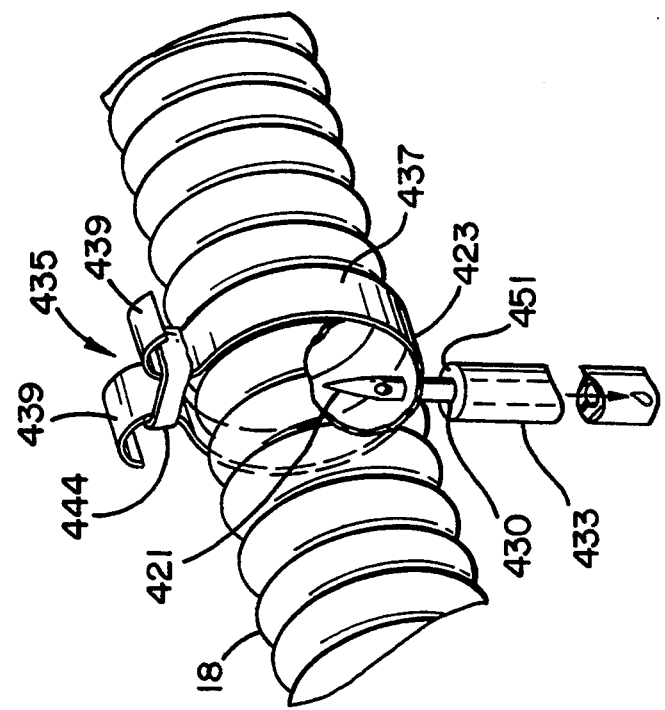
FIG. 6 is a partial cutaway perspective view of a modification of the invention.

FIG. 6 is a perspective cutaway view of an additional feature of the modification of the respiratory support system 10. The condensate conduit 433 is similar to the condensate conduit illustrated in FIG. 5, including a probe or spike 421, having an inlet hole 423, and a sealing connection 430 between condensate conduit 433 and spike 421.

The embodiment shown in FIG. 6 further includes a retention assembly 435 for maintaining the spike 421 in position so that the inlet hole 423 of spike 421 is within, but closely adjacent to the bottom portion of, the corrugated tubing wall of inhalation conduit 18. Retention assembly 435 includes a strap 437 having two opposing upturned ends 439. The strap 437 surrounds the corrugated tubing of the inhalation conduit 18, and the two opposing ends 439 are disposed adjacent one another. The ends 439 can then be secured to retain the strap 437 around conduit 18 by use of an appropriate fastener, such as a rubber band 441.

Figure 7:
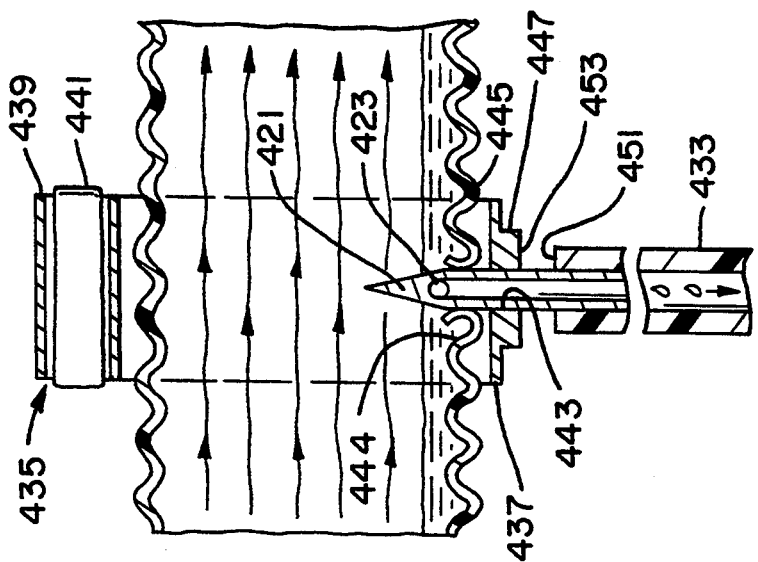
FIG. 7 is a cross-sectional view of the modification according to FIG. 6.

FIG. 7 illustrates in cross section the structure of the condensate conduit 433, spike 421 and strap 437 which surrounds inhalation conduit 18 and which is shown mostly in phantom. The strap 437 and spike 421 are illustrated as being attached to each other through a hole 443 in strap 437 by means of an adhesive or by friction fit. The extent to which the spike 421 extends through hole 443 in strap 437 is a critical parameter, and especially the height of the inlet hole 423 from the inside surface 445 of the strap 437. During placement of the spike 421 into inhalation conduit 18, the hole 423 must be within the inside wall 444 of inhalation conduit 18 so as to permit the condensed water to drain through the inlet hole 423 and into condensate conduit 433. However, if the inlet hole 423 is too far from the inside wall 444 of inhalation conduit 18 because it overly extends into the space defined by the inhalation conduit 18, it will be ineffective to drain a substantial amount of water which condenses in inhalation conduit 18 and the water will become am impediment to air flow through the conduit.

One manner in which the spike is limited to extending only the desired distance into the conduit is to use a cone-shaped spike 421, as shown in FIG. 7. The expanding diameter of the cone shape of the spike 421 as it is pushed through hole 443 in an abutment member 447 disposed on strap 437 will cause spike 421 to stop at the appropriate place when the angular sidewall of the cone and the diameter of the hole 443 meet. By preselecting the taper of the spike the expanding diameter of spike 421 will reach the limit of the diameter of hole 443, and the spike 421 and hole 443 will provide friction fit surfaces to maintain the spike 421 at a set distance within the bottom tube wall of inhalation conduit 18, as shown in FIG. 7.

Alternatively, the termination of the conduit 433 at surface 451 can create a stop at a surface 453 of abutment member 447. The meeting of the surfaces 451 and 453 will provide a predetermined distance of the protrusion of spike 421 and hole 423 beyond the inside wall 444 of inhalation conduit 18. The relative position of the hole 423 from the conduit termination surface 451 can be made adjustable simply by pushing the spike 421 deeper within or pulling the spike 421 out of the condensate conduit 433. This adjustability provides a means for adjusting the predetermined distance which the hole 423 of spike 421 extends beyond the inside wall 444 of the inhalation line 18, and ensures that the hole 423 will be positioned within the pool of condensate water formed with the inhalation conduit 18.

In system 10, in any of the described variations, the pressure in the inhalation conduit 18 may vary from atmospheric to a peak pressure 45 (FIG. 2); the peak pressure usually reaches about twenty centimeters of water during the inhalation portion 42 of the breathing cycle, but may vary substantially. The temperature in conduit 18 is typically about 125° F., with 100% humidity. Pressure conditions in the exhalation conduit 22 are similar, but with an appreciably lower peak pressure. The entire system may be maintained above atmospheric at all times, in some instances such as those used to aid victims of emphysema.

I claim:

1. A condensation collector for removing condensate of predetermined density from the inhalation and exhalation conduits of a respiratory support system comprising: a ventilator/humidifier apparatus having a fresh air make-up inlet, a return inlet, and an outlet, an inhalation conduit for connecting the ventilator/humidifier outlet to a patient, an exhalation conduit for connecting the patient back to the ventilator/humidifier return inlet, and a condensate discharge connection connected to each of the conduits, the condensation collector comprising:

a condensate container having an inlet adjacent the top of the container;

a collection chamber having an inlet and a bottom outlet connected to the condensate container inlet;

a valve housing in fluid communication with said collection chamber inlet having two inlets and a pressure actuated valve operatively positioned within said valve housing providing means to selectively permit discharge from said discharge connections of said conduits;

two condensate conduits each having two ends the first of said ends being respectively connected to one said condesate discharge connections and the second of Said respective ends each attached to an inlet of said valve housing;

a buoyant valve closure member, having a density less than said predetermined density, disposed within the collection chamber for movement between a closed position in which the closure member closes the bottom outlet of the collection chamber and an open position in which the closure member floats on accumulated condensate above the bottom outlet.

2. A condensation collector for a respiratory support system according to claim 1 in which the valve closure member has the configuration of a ball.

3. A condensation collector for a respiration system according to claim 2 and further comprising:

a valve closure member guide extending radially across the collection chamber and having a central aperture, aligned with and encompassing the central part of the valve closure member when that member is in its closed position.

4. A condensation collector for a respiratory support system according to claim 2 and further comprising:

an O-ring mounted in the bottom of the collection chamber in encompassing relation to the chamber outlet:

the O-ring affording a valve seat for the valve closure member.

5. A condensation collector for a respiratory support system according to claim 2, and further comprising a valve seat for the valve closure member comprising:

a disc of flexible material mounted in the bottom of the collection chamber and having a central aperture aligned with the chamber outlet.

6. A condensation collector for a respiratory support system according to claim 2 in which the valve closure member is a ping-pong ball.

7. A respiratory support system comprising:

ventilator/humidifier apparatus having an inlet, a return, and an outlet:

an inhalation conduit, comprising a corrugated hose, for connecting the ventilator/humidifier outlet to a patient;

an exhalation conduit, comprising a corrugated hose, for connecting the patient back to the ventilator/humidifier return;

at least one condensate discharge connection connected to a low point in one of the inhalation or exhalation conduits, said conduit discharge connection comprising a probe defining means for inserting Said condensate discharge connection a predetermined distance into one of said inhalation or exhalation conduits during operation of said respiratory support system;

a condensate container having an inlet adjacent the top of the container;

a collection chamber having a bottom outlet connected to the condensate container inlet;

a buoyant valve closure member, having a density less than said predetermined density, disposed within the collection chamber for movement between a closed position in which the closure member closes the bottom outlet of the collection chamber and an open position in which the closure member floats on accumulated condensate above the bottom outlet;

and a condensate conduit for connecting said condensate discharge connection to the collection chamber, above the valve closure member.

8. The respiratory support system of claim 7 wherein duplicate condensate discharge connections are provided one of which is respectively connected to each of the inhalation and exhalation conduits and wherein there is provided duplicate condensate conduits for connecting each of the condensate discharge connections to the collection chamber.

9. The respiratory support system of claim 7 wherein said conduit discharge connection is secured to said inhalation or exhalation conduits by a strap encircling said conduit having a hole therethrough for passage of said probe of said conduit discharge connection.

10. The respiratory support system of claim 9 wherein said strap includes opposing upturned ends disposed adjacent to one another.

11. The respiratory support system of claim 10 wherein said upturned ends are secured by a fastener to retain said strap around said conduit.

12. A respiratory support system according to claim 7 in which the valve closure member has the configuration of a ball.

13. A respiratory support system according to claim 12 and further comprising:

an O-ring mounted in the bottom of the condensate collection chamber in encompassing relation to the chamber outlet;

the O-ring affording a valve seat for the valve closure member.

14. A respiratory support system according to claim 12 and further comprising:

a valve closure member guide extending across the collection chamber and having a central aperture, aligned with and encompassing the central part of the valve closure member when that member is in its closed position.

15. A condensation collector for a respiratory support system according to claim 12 in which the valve closure member is a ping-pong ball.

16. A condensation collector for a respiratory support system according to claim 12, and further comprising a valve seat for the valve closure member comprising:

a disc flexible material mounted in the bottom of the collection chamber and having a central aperture aligned with the chamber outlet.

17. A condensation collector for a respiratory support system according to claim 16 in which the valve seat material is an elastomer.

* * * * *